US00PP16345P2

(12) United States Plant Patent
Murakami

(10) Patent No.: US PP16,345 P2
(45) Date of Patent: Mar. 14, 2006

(54) ***SCOPARIA* PLANT NAMED 'SUNTUTUKI'**

(50) Latin Name: ***Scoparia* sp.**
Varietal Denomination: Suntutuki

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 44 days.

(21) Appl. No.: 11/036,732

(22) Filed: Jan. 14, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS http://www.rain–tree.com/vassourinha.htm.*
http://www.naturehills.com/new/product.annualdetails.*
http://plants.usda.gov/cgi_bin/plant_profile cgi? symbol= SCDU3.*

* cited by examiner

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Scoparia* plant named 'Suntutuki', characterized by its upright, mounded and outwardly spreading plant habit; freely branching growth habit; very freely flowering habit; small yellow-colored flowers; flowering continuous from spring to late autumn; and good garden performance.

1 Drawing Sheet

Botanical designation: *Scoparia* sp.
Cultivar denomination: 'Suntutuki'.

BACKGROUND OF THE INVENTION

The present Invention relates to a new and distinct cultivar of *Scoparia* plant, botanically known as *Scoparia* sp., and hereinafter referred to by the cultivar name Suntutuki.

The new *Scoparia* is a product of a planned breeding program conducted by the Inventor in Yokaichi, Shiga, Japan. The objective of the breeding program is to create new freely-branching *Scoparias* with numerous flowers and attractive flower coloration.

The new *Scoparia* originated from a cross-pollination made by the Inventor in July, 2000 of a proprietary selection of *Scoparia* sp. identified as code number SC6, not patented, as the female, or seed, parent with a proprietary selection of *Scoparia* sp. identified as code number SC7, not patented, as the male, or pollen, parent. The new *Scoparia* was selected as a single plant from the resulting progeny of the cross-pollination by the Inventor in a controlled environment in Yokaichi, Shiga, Japan.

Asexual reproduction of the new cultivar by terminal cuttings in a controlled environment in Yokaichi, Shiga, Japan since November, 2002, has shown that the unique features of this new *Scoparia* are stable and reproduced true to type in successive generations.

SUMMARY OF THE INVENTION

Plants of the cultivar Suntutuki have not been observed under all possible environmental conditions. The phenotype may vary somewhat with variations in environment such as temperature and light intensity without, however, any variance in genotype.

The following traits have been repeatedly observed and are determined to be the unique characteristics of 'Suntutuki'. These characteristics in combination distinguish 'Suntutuki' as a new and distinct cultivar of *Scoparia:*

1. Upright, mounded and outwardly spreading plant habit.
2. Freely branching growth habit.
3. Very freely flowering habit.
4. Small yellow-colored flowers.
5. Flowering continuous from spring to late autumn.
6. Good garden performance.

Plants of the new *Scoparia* can be compared to plants of the parent selections. In side-by-side comparisons conducted in Yokaichi, Shiga, Japan, plants of the new *Scoparia* were larger and had larger flowers than plants of the female parent selection. In side-by-side comparisons conducted in Yokaichi, Shiga, Japan, plants of the new *Scoparia* were more upright, had shorter internodes and were more freely branching than plants of the male parent selection.

Plants of the new *Scoparia* can be compared to plants of the cultivar, W1, not patented. In side-by-side comparisons conducted in Yokaichi, Shiga, Japan, plants of the new *Scoparia* differed from plants of the cultivar W1 in the following characteristics:

1. Plants of the new *Scoparia* were larger and more vigorous than plants of the cultivar W1.
2. Plants of the new *Scoparia* had smaller leaves than plants of the cultivar W1.
3. Plants of the new *Scoparia* were more freely flowering than plants of the cultivar W1.
4. Plants of the new *Scoparia* had larger flowers than plants of the cultivar W1.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Scoparia*.

The photograph at the top of the sheet is a side perspective view of a typical plant of 'Suntutuki'.

The photograph at the bottom of the sheet is a close-up of a flowering stem of 'Suntutuki'.

DETAILED BOTANICAL DESCRIPTION

The aforementioned photographs and following observations and measurements describe plants grown in Yokaichi, Shiga, Japan in a polyethylene-covered greenhouse during the autumn with day temperatures averaging 25° C. and night temperatures averaging 15° C. Plants were grown in 15-cm container and had been growing for about eight months when the photographs and description were taken. Color references are made to The Royal Horticultural Society Colour Chart, 2001 Edition, except where general terms of ordinary dictionary significance are used.

Botanical classification: *Scoparia* sp. cultivar Suntutuki.

Parentage:

*Female parent.*—Proprietary selection of *Scoparia* sp. identified as code number SC6, not patented.

*Male parent.*—Proprietary selection of *Scoparia* sp. identified as code number SC7, not patented.

Propagation:

*Type cutting.*—Vegetative cuttings.

*Time to initiate roots.*—About six days at 20 to 25° C.

*Time to produce a rooted young plant.*—About three weeks at 20 to 25° C.

*Root description.*—Fine, fibrous, fleshy; light brown in color.

*Rooting habit.*—Freely branching.

Plant description:

*Form.*—Upright, mounded and outwardly spreading plant habit. Freely branching growth habit with lateral branches forming potential at every node. Vigorous growth habit.

*Fragrance.*—Similar to red licorice.

*Plant height.*—About 12.2 cm.

*Plant diameter.*—About 23.8 cm.

*Lateral branches.*—Length: About 17 cm. Diameter: About 0.8 mm. Internode length: About 1.2 cm. Strength: Strong. Texture: Smooth, glabrous. Color: 146C.

*Foliage description.*—Arrangement: Whorled, ternate; simple. Length: About 1.6 cm. Width: About 1 mm. Shape: Pinnately lobed. Apex: Acute. Base: Cuneate. Margin: Entire; lobed. Texture, upper and lower surfaces: Pubescent; hairs very short. Venation pattern: Pinnate. Color: Developing and fully expanded foliage, upper surface: 146A; venation, 146A. Developing and fully expanded foliage, lower surface: 146C; venation, 146C. Petiole: Length: About 6 mm. Diameter: About 0.8 mm. Color: 146A.

Flower description:

*Flower type and habit.*—Solitary axillary star-shaped flowers; typically three per node. Flowers not persistent. Flowers face upright or outwardly. Very freely flowering habit.

*Natural flowering season.*—Plants flower from spring to late autumn in Japan; flowering continuous during this period.

*Flower longevity on the plant.*—About three days.

*Fragrance.*—None detected.

*Flower size.*—Length: About 1.2 cm. Width: About 5.8 mm. Depth: About 6 mm.

*Flower buds.*—Length: About 5 mm. Diameter: About 2.4 mm. Shape: Ovoid. Color: 143C.

*Petals.*—Quantity/arrangement: Four petals in a single whorl; fused at the base. Length: About 6 mm. Width: About 5 mm. Shape: Rhomboidal. Apex: Acute. Base: Fused. Margin: Entire. Texture, upper and lower surfaces: Smooth, satiny. Color: When opening, upper and lower surfaces: 5A. Fully opened, upper and lower surfaces: 5A.

*Sepals.*—Arrangement/appearance: Single whorl of five sepals; fused at the base. Length: About 3.5 mm. Width: About 1.4 mm. Shape: Lanceolate. Apex: Acute. Base: Fused. Margin: Entire. Texture, upper and lower surfaces: Smooth, glabrous. Color, upper and lower surfaces: 143C.

*Peduncles.*—Length: About 1.1 cm. Width: About 0.2 mm. Angle: About 45° from stem axis. Strength: Strong. Texture: Pubescent. Color: 143C.

*Reproductive organs.*—Stamens: Quantity per flower: Four. Anther shape: Ovoid. Anther length: About 0.5 mm. Anther color: 5A. Pollen amount: Moderate. Pollen color: 5A. Pistils: Quantity per flower: One. Style color: 5A. Stigma shape: Oblong. Stimga color: 149A. Ovary color: 151C.

*Fruit/seed.*—Fruit and seed production has not been observed.

Disease/pest resistance: Plants of the new *Scoparia* have not been noted to be resistant to specific pathogens or pests common to *Scoparia*.

Garden performance: Plants of the new *Scoparia* have been observed to have good garden performance and tolerate rain, wind and tolerated temperatures from −1 to 35° C.

It is claimed:

1. A new and distinct cultivar of *Scoparia* plant named 'Suntutuki', as illustrated and described.

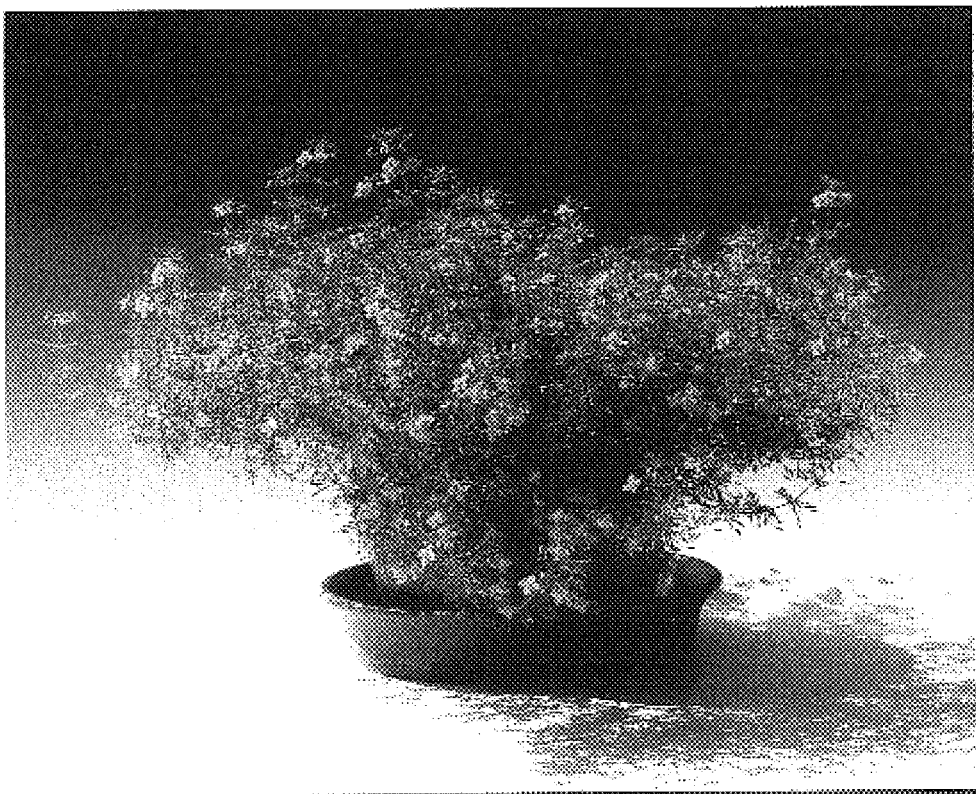
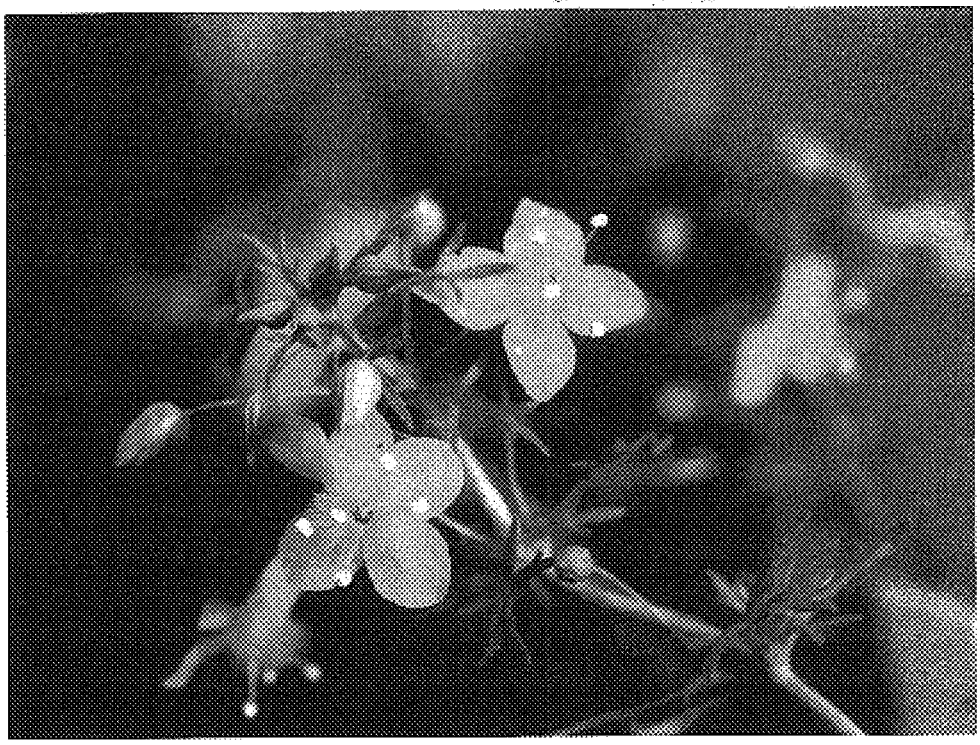

* * * * *